(12) United States Patent
Managoli

(10) Patent No.: US 7,378,112 B2
(45) Date of Patent: May 27, 2008

(54) HERBAL COMPOSITION TO IMPROVE PSYCHOLOGICAL FUNCTIONS AS AN ANXIOLYTIC, TRANQUILIZER, AND NON-NARCOTIC SEDATIVE, AS WELL AS OTHER PHYSIOLOGICAL FUNCTIONS

(75) Inventor: Nandkishor Bapurao Managoli, Surat (IN)

(73) Assignee: Sahajanand Biotech Pvt. Ltd., Surat, Gujarat (IN)

( * ) Notice: Subject to any disclaimer, the term of this patent is extended or adjusted under 35 U.S.C. 154(b) by 14 days.

(21) Appl. No.: 11/287,737

(22) Filed: Nov. 28, 2005

(65) Prior Publication Data

US 2007/0122495 A1    May 31, 2007

(51) Int. Cl.
*A61K 36/84* (2006.01)
*A61K 36/00* (2006.01)

(52) U.S. Cl. ...................... 424/725; 424/773

(58) Field of Classification Search .............. None
See application file for complete search history.

(56) References Cited

U.S. PATENT DOCUMENTS 6,080,401 A * 6/2000 Reddy et al. .............. 424/93.3

2003/0091553 A1 * 5/2003 Gehlsen ..................... 424/94.4
2006/0159784 A1 * 7/2006 Ghosal ...................... 424/762

FOREIGN PATENT DOCUMENTS

GB     2314270       * 12/1997
ZA     200103250 A   * 12/2001

\* cited by examiner

*Primary Examiner*—Patricia Leith
(74) *Attorney, Agent, or Firm*—Volpe and Koenig, P.C.

(57) ABSTRACT

A pharmaceutical or medicinal preparation comprising a mixture of herbs including *Bacopa monniera, Convolvulus pluricaulis, Nardostachys jatamansi, Valerian wallichi, Myristica fragrans, Centella asiatica, Withania somnifera, Ocimum sanctum, Acorus calamus, Boerhavia diffusa* and *Tinospora cordifolia* or a mixture of the active ingredients that have been extracted from such herbs for treatment of conditions involving hormone imbalances, circulatory conditions, musculo-skeletal problems, gastrointestinal problems, psychological conditions, sleep disorders, and problems in the nervous system among others.

4 Claims, No Drawings

HERBAL COMPOSITION TO IMPROVE PSYCHOLOGICAL FUNCTIONS AS AN ANXIOLYTIC, TRANQUILIZER, AND NON-NARCOTIC SEDATIVE, AS WELL AS OTHER PHYSIOLOGICAL FUNCTIONS

FIELD OF INVENTION

This invention relates to a novel herbal formulation that has been found to be effective for a range of psychological, pathological, and physiological conditions involving many systems in the human body. The present invention relates particularly to an herbal composition comprising a blend of extracts and their active ingredients that are effective for the treatment of conditions involving hormone imbalances, circulatory conditions, musculo-skeletal problems, gastrointestinal problems, immune system conditions, psychological conditions, sleep disorders, and problems in the nervous system among others.

BACKGROUND

Various psychological, pathological, and physiological conditions of the human body are conventionally treated or regulated using drugs. Such treatments include chemically synthesized preparations, or other therapies, including radiation or chemotherapy, which often have adverse side effects. These drugs and therapies address the medical problem with carrying degrees of effectiveness, but often overlook one of the most important factors in treatment: psychological well-being. A well-rested, optimistic, and upbeat person has a better chance of recovery or quality of life than a tired, depressed, and angry patient. Further, many drugs and therapies adversely affect a patient with unwanted and unwelcome side effects.

There is a need for improved medicinal preparations for use in the treatment or regulation of the aforementioned conditions, without the adverse effects associated with conventional modes of treatment. It is an object of the present invention to provide such a preparation.

SUMMARY

The present invention is directed to a pharmaceutical or medicinal preparation comprising a mixture of herbs including *Bacopa monniera, Convolvulus pluricaulis, Nardostachys jatamansi, Valerian wallichi, Myristica fragrans, Centella asiatica, Withania somnifera, Ocimum sanctum, Acorus calamus, Boerhavia diffusa* and *Tinospora cordifolia* or a mixture of the active ingredients that have been extracted from such herbs for treatment of conditions involving hormone imbalances, circulatory conditions, musculo-skeletal problems, gastrointestinal problems, psychological conditions, sleep disorders, and problems in the nervous system among others.

One aspect of the present invention is directed to a pharmaceutical or medicinal composition comprising: *Bacopa monniera* in the amount of 08-12% by weight of the composition, preferably 10%; *Convolvulus pluricaulis* in the amount of 08-12% by weight of the composition, preferably 10%; *Nardostachys jatamansi* in the amount of 08-12% by weight of the composition, preferably 10%; *Valerian wallichi* in the amount of 08-12% by weight of the composition, preferably 10%; *Myristica fragrans* in the amount of 08-12% by weight of the composition, preferably 10%; *Centella asiatica* in the amount of 08-12% by weight of the composition, preferably 10%; *Withania somnifera* in the amount of 08-12% by weight of the composition, preferably 10%; *Ocimum sanctum* in the amount of 08-12% by weight of the composition, preferably 10%; *Acorus calamus* in the amount of 08-12% by weight of the composition, preferably 10%; *Boerhavia diffusa* in the amount of 04-06% by weight of the composition, preferably 05%; and *Tinospora cordifolia* in the amount of 04-06% by weight of the composition, preferably 05%.

DETAILED DESCRIPTION OF THE PREFERRED EMBODIMENT(S)

The following invention provides a pharmaceutical or medicinal preparation that comprises the following herb mixture: *Bacopa monniera, Convolvulus pluricaulis, Nardostachys jatamansi, Valerian wallichi, Myristica fragrans, Centella asiatica, Withania somnifera, Ocimum sanctum, Acorus calamus, Boerhavia diffusa* and *Tinospora cordifolia* or a mixture of the active ingredients that have been extracted from such herbs, or chemically synthesized therefrom.

The ingredients and preferred proportions of herbs in the herbal formulation according to the present invention are set forth in Table 1. It should be understood that the proportions of individual herbs may vary. In particular, the proportions of one or more of the components may vary in order to optimize the treatment effects to suit individual patients.

TABLE 1

| BOTANICAL NAME | COMMON NAME | PART USED | BIO MARKERS | PERCENT BY WEIGHT |
| --- | --- | --- | --- | --- |
| *Bacopa monnieri* | Bacopa | Herb | Bacosides 15%-50% Alkaloids 5% | 10% |
| *Convolvulus pluricaulus* | Field bindweed | Plant | Bitters >2.5% | 10% |
| *Nardostachys jatamansi* | Indian valerian | Root | Vol. Oil 0.1%-0.5% | 10% |
| *Valerian wallichi* | Scouler's valerian | Root | Valeric acid 0.8% | 10% |
| *Myristica fragrans* | Nutmeg | Fruit | Vol. Oil 4% | 10% |
| *Centella asiatica* | Gotu kola | Herb | Asiaticosides >10% Asiatic acid 2% | 10% |
| *Withania somnifera* | Ashwagandha | Root | Withanolides >2.5% | 10% |
| *Ocimum sanctum* | Holi basli | Herb | Tannins >7% Ursolic acid >2% | 10% |
| *Acorus calamus* | Calamus | Rhizome | Vol. Oil 1% | 10% |
| *Boerhavia diffusa* | Boerhavia | Root | Alkaloids 0.01%-0.08% | 5% |
| *Tinospora cordifolia* | Indian tinospora | Root | Bitter >1.5% | 5% |

An important aspect of the invention is the combination of these herbs and extracts, which provide more benefit than a single herb. This unexpected synergy between the herbs exhibits the beneficial pharmacological effects, with minimal or no adverse toxic reactions. An additional advantage of this multi-herb formula is that it minimizes the risk of a patient developing drug resistance.

The herbal combination described herein exhibits various beneficial effects and is particularly useful in a spectrum of physiological, pathological, and physiological conditions in humans, especially in psychologically affected individuals. These most beneficial effects include:

(a) Anxiolytic;
(b) Adaptogenic (ability to adapt to stress);
(c) Antistress;
(d) Nervine tonic (improves alertness and stabilizes the nerves);
(e) Antiulcerogenic (prevents stress induced ulcers in the stomach);
(f) Tranquilizing effect (calming and soothing effect, inducing good sleep and preventing episodes of hysteria);
(g) Mild sedative effect (inducing good sleep, relieving tension-headaches, palpitations);
(h) Smooth muscle relaxant (improving bowel habits, restoring normal respiratory pattern);
(i) increased sexual activity; and
(j) Immunostimulant.

The manufacture of an herbal composition and treatment with an herbal composition according to the present invention will now be illustrated by the following example. However, it will be appreciated by one of ordinary skill in the art that the proportions of ingredients, amount of ingredients, and form of administration can vary without departing from the spirit of this invention.

A polyherbal formulation was prepared in accordance with the present invention by harvesting and cleaning each of the raw herbal ingredients, grinding each ingredient to a fine powder form, diluting each ingredient, and subjecting each of the herbal ingredients to standard solvent extraction methods, including alcoholic and hydroalcoholic solvent extraction, Freon gas extraction, $CO_2$ gas extraction, or any other suitable extraction method.

By way of illustration only, the extraction can be performed by using volatile Freon gas. This process has the advantage of being fast and also has the ability to preserve the active chemicals (alkaloids, non-alkaloids, electrolytes, minerals, etc.) in their natural form (as it does not involve heating and denaturation at any stage of the process). Freon, being a highly volatile compound with its boiling point at −21° C., evaporates totally after extraction yielding an ultrapure concentrate of the herbal ingredients.

After extraction, the concentrated extracts were recovered, filtered, and dried. The herbal ingredients were then mixed in the following proportions:

TABLE 2

| BOTANICAL NAME | PERCENT BY WEIGHT | Mg/capsule |
| --- | --- | --- |
| *Bacopa monnieri* | 10% | 75 mg |
| *Convolvulus pluricaulus* | 10% | 75 mg |
| *Nardostachys jatamansi* | 10% | 75 mg |
| *Valerian wallichi* | 10% | 75 mg |
| *Myristica fragrans* | 10% | 75 mg |
| *Centella asiatica* | 10% | 75 mg |
| *Withania somnifera* | 10% | 75 mg |
| *Ocimum sanctum* | 10% | 75 mg |
| *Acorus calamus* | 10% | 75 mg |
| *Boerhavia diffusa* | 5% | 37.5 mg |
| *Tinospora cordifolia* | 5% | 37.5 mg |

After mixing the ingredients in the specified quantities, the premix was blended in an automatic blender in order to prepare a homogeneous mixture.

The blended and homogenized herbal mixture was filled in gelatin capsules in quantities of 750 milligrams each (to standardize the dosage to one capsule twice or thrice a day).

It will be appreciated by one of ordinary skill in the art that the amount of the herbal composition per capsule may vary depending on the individual, the condition being treated, or the frequency of dosage. It will be further understood by one of ordinary skill in the art that the herbal preparation according to the present invention can be administered in accordance with any conventional form of administration, including, without limitation, a liquid or syrup, capsule, or tablet.

Toxicity Tests

Acute oral toxicity was conducted using Sprague Dawley rats by administering them the herbal medicine. A single loading dose of 2000 mg/kg body weight was given to the rats to assess its effects on the rats. No signs of toxicity were observed, and there were no instances of mortality in any of the rats treated with the formulation.

Human Clinical Trials (1) Case Report of Premenstrual Syndrome and Premenstrual Dysphoric Disorder The patient was a female aged 34 years diagnosed with premenstrual dysphoric disorder with aggravated symptoms such as depression, edema, lack of enthusiasm, suicidal tendencies, loss of sexual drive, general apathy to surroundings, irritability, etc. experienced cyclically with the menstrual cycle. The patient was also experiencing chronic fatigue, malaise, loss of appetite, anorexia, loss of weight and anxiety before initiation of herbal therapy.

The patient was reluctant to receive conventional antidepressant therapy because of the hypersensitivity to these drugs and voluntarily acceded to take herbal therapy.

Herbal therapy using the above inventive remedy, taking three 750 mg capsules daily, began in October 2004 after completing the baseline tests like complete hemogram, hepatic, and renal profiles along with radiological studies to detect occult disease, if any. The patient was examined and followed up with on a monthly basis to monitor her progress.

The patient experienced marked changes and improvement in quality of life after completion of one month of therapy taking the herbal mixture. The patient gained her appetite, vigor, enthusiasm, gained 1.0 kg weight and also reported alleviation of anxiety, depression, stress, suicidal thoughts and regained enthusiasm in routine activities.

Her sleep pattern was restored to normalcy, fatigue was reduced and a positive thought process was initiated, inducing the patient to believe in herself and her convictions.

The patient's latest report was prepared in June 2005 and showed a marked improvement in all parameters related to quality of life. Her weight gain in 8 months has been 2.2 kg., appetite is good, there is no complaint of fatigue, or malaise, or anxiety. Hemoglobin has improved by 2.1 gm % and has been stable at a level of 13.2 gm % over the previous 3 months.

The positive therapeutic effects are directly attributable to the herbal composition using the present invention.

(2) Case Report of the Utility of the Herbal Formulation as an Anxiolytic, Antistress A senior marketing executive in a leading company dealing in sanitary ware was under stress and experienced anxiety spells due to the ever-growing sales targets which he could not achieve. This stress led to symptoms like palpitations, tremors, sleeplessness, and loss of concentration, irritability, diarrhea due to increased bowel movements, high blood pressure and tension headaches. He also complained of hyperacidity with pain in the epigastric region which was relieved by antacids.

The inventive herbal formulation was administered orally from April 2004 and the executive has been using it daily through the present with effective results. The patient began to sleep peacefully at night because of the antistress and tranquiliser effects and wake up with a fresh, positive attitude which in turn improved his work efficiency. Blood pressure normalized because of the anxiolytic and adaptogenic effects. Hyperacidity and stress-ulcers, tension headaches, irritability and hypermotility of the bowels reduced because of the antistress effects. Thus there has been a marked improvement in the psychological status of the person, which is reflected in his improved work efficiency. Thus there is an obvious improvement in his quality of life.

(3) Case Report of Depression

A middle aged lady experienced symptoms of endogenous depression like crying spells, loss of appetite and weight, suicidal tendencies and loss of sexual drive which aggravated over a period of 6-8 months before she went to a psychiatrist for advice. She was diagnosed with endogenous depression and immediately put on conventional antidepressants. However, the lady could not perform her routine activities optimally because of the strong sedative effects of the conventional therapy.

She was willing to try the inventive herbal formulation and was put on this therapy initially from March 2005 for a period of three months. She opted to stop conventional therapy after consultations with her psychiatrist.

The first signs of improvement were evident after one week of therapy when she realized that the frequency of her crying spells reduced drastically. Her appetite increased and weight increased by 1.0 kg after one and a half months of herbal therapy. Libido improved and suicidal tendencies were absent after completion of three months of therapy. No adverse effects were noted. She was asked to stop the therapy for a month and follow up after that period. It was observed that some of the symptoms returned following cessation of the therapy. The therapy was restarted, and presently there is a marked improvement in all the symptoms. The lady continues to receive the inventive herbal therapy and has not complained of any adverse effects.

(4) Case Report of Schizophrenia

A young, intelligent and sensitive doctor with a post graduate degree in Physiology and a family history of multiple suicides in the family was diagnosed as suffering from Schizophrenia when he once attempted suicide because he could not get grades in his exams up to his expectations. He appeared extremely happy and joyful at times, and was extremely upset and withdrawn at others. His mood swings were characteristic of the split personality descriptions in the texts.

Herbal therapy was initiated 2 years after the first diagnosis because he attempted suicide the second time in December 2003. It was noted that the extreme mood swings reduced and he remained relatively stable psychologically after 3 months of therapy. The patient is continuing to receive this therapy and he is more at peace with himself and now finds life more meaningful.

(5) Case Report of Manic Depression

A known case of manic depression on Lithium carbonate therapy for 5 years wanted to stop conventional therapy due to the toxic side effects of the drug. The inventive herbal therapy was initiated after procuring informed consent. Symptoms like crying spells, hysteria, suicidal tendencies subsided after starting the herbal therapy and discontinuing Lithium carbonate.

Eight months after initiation of therapy, the patient is stable, proving the efficacy of this herbal therapy.

It will be appreciated to those of ordinary skill in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed is:

1. A pharmaceutical or medicinal mixture of herbal extracts comprising:
   Bacopa monniera extract comprising 15.0%-50.0% by weight bacosides and 5.0% by weight alkaloids;
   Convolvulus pluricaulis extract comprising greater than 2.5% by weight bitters;
   Nardostachys jatamansi root extract comprising 0.1%-0.5% by weight volatile oil;
   Valerian wallichi extract comprising 0.8% by weight valeric acid;
   Myristica fragrans extract comprising 4.0% by weight volatile oil;
   Centella asiatica extract comprising greater than 10.0% by weight asiaticosides and 2.0% asiatic acid;
   Withania somnifera root extract comprising greater than 2.5% by weight withanolides;
   Ocimum sanctum extract comprising greater than 7.0% by weight tannins and greater than 2.0% by weight ursolic acid;
   Acorus calamus extract comprising 1.0% by weight volatile oil;
   Boerhavia diffusa root extract comprising 0.01%-0.08% by weight alkaloids; and
   Tinospora cordifolia root extract comprising greater than 1.5% by weight bitters.

2. The pharmaceutical or medicinal mixture of claim 1, wherein the mixture comprises:
   Bacopa monniera extract in the amount of 08-12% by weight of the composition;
   Convolvulus pluricaulis extract in the amount of 08-12% by weight of the composition;
   Nardostachys jatamansi root extract in the amount of 08-12% by weight of the composition;
   Valerian wallichi extract in the amount of 08-12% by weight of the composition;
   Myristica fragrans extract in the amount of 08-12% by weight of the composition;
   Centella asiatica extract in the amount of 08-12% by weight of the composition;
   Withania somnifera root extract in the amount of 08-12% by weight of the composition;
   Ocimum sanctum extract in the amount of 08-12% by weight of the composition;
   Acorus calamus extract in the amount of 08-12% by weight of the composition;
   Boerhavia diffusa root extract in the amount of 04-06% by weight of the composition; and
   Tinospora cordifolia root extract in the amount of 04-06% by weight of the composition.

3. The pharmaceutical or medicinal mixture of claim 1, wherein the mixture comprises:
   Bacopa monniera extract in the amount of 10% by weight of the composition;
   Convolvulus pluricaulis extract in the amount of 10% by weight of the composition;
   Nardostachys jatamansi root extract in the amount of 10% by weight of the composition;
   Valerian wallichi extract in the amount of 10% by weight of the composition;

*Myristica fragrans* extract in the amount of 10% by weight of the composition;
*Centella asiatica* extract in the amount of 10% by weight of the composition;
*Withania somnifera* root extract in the amount of 10% by weight of the composition;
*Ocimum sanctum* extract in the amount of 10% by weight of the composition;
*Acorus calamus* extract in the amount of 10% by weight of the composition;
*Boerhavia diffusa* root extract in the amount of 5% by weight of the composition; and
*Tinospora cordifolia* root extract in the amount of 5% by weight of the composition.

4. The pharmaceutical or medicinal herbal mixture of claim 1, wherein the mixture is in the form of at least one of the group consisting of a gelatin capsule, a tablet, a liquid and a syrup.

* * * * *